United States Patent [19]

Elam

[11] 4,134,407
[45] Jan. 16, 1979

[54] EXTERNAL PRESSURE-VOLUME MONITOR FOR ENDOTRACHEAL CUFF

[76] Inventor: James O. Elam, 6723 S. Euclid, Chicago, Ill. 60649

[21] Appl. No.: 781,177

[22] Filed: Mar. 25, 1977

[51] Int. Cl.$^2$ .............................................. A61M 25/00
[52] U.S. Cl. .................................... 128/351; 116/270; 116/DIG. 8
[58] Field of Search ................................ 128/348–351; 116/114 PV, DIG. 8, DIG. 9

[56] References Cited

U.S. PATENT DOCUMENTS

| | | | |
|---|---|---|---|
| 3,407,817 | 10/1968 | Galleher | 128/351 |
| 3,731,692 | 5/1973 | Goodyear | 128/351 |
| 3,978,863 | 9/1976 | Fettel et al. | 128/349 B |
| 4,016,885 | 4/1977 | Bruner | 128/349 B |

FOREIGN PATENT DOCUMENTS 2313084  12/1976  France .................................. 128/349 B

*Primary Examiner*—Dalton L. Truluck
*Attorney, Agent, or Firm*—Hosier, Niro & Daleiden, Ltd.

[57] ABSTRACT

A monitoring system is comprised of an elastomer balloon housed in a rigid cage having a plurality of windows which is designed to continuously indicate the state of collapse or expansion of the internal cuff or cuffs of an encotracheal tube. This balloon monitor is interconnected in series with the pneumatic channel through which the cuff or cuffs are inflated. The volume of the balloon may be observed visually with reference to its filling the cage enclosure denoting thereby its state of inflation and therefore, also that of the endotracheal cuff. Calibration of the balloon monitor provides means for accurately observing both the volume and pressure of air in the system. Therefore, visual inspection of the balloon monitor indicates by reason of the calibration the prevailing level of pressure in the patient's endotracheal cuff. Since the maintenance of safe cuff pressures results in a normal position of the balloon, in contact with the cage, electrical and electronic means may be arranged appropriately between the balloon and the inner surface of the cage to produce a warning signal in the event of cuff overdistension and an alarm signal in the event of cuff collapse.

4 Claims, 8 Drawing Figures

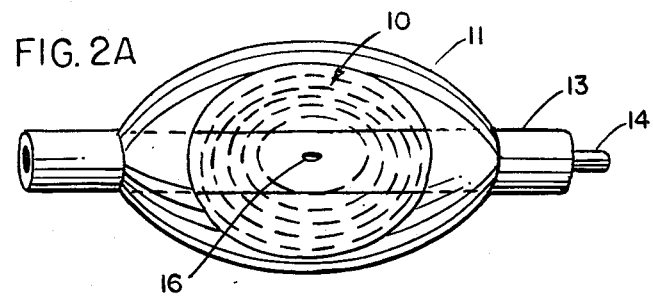
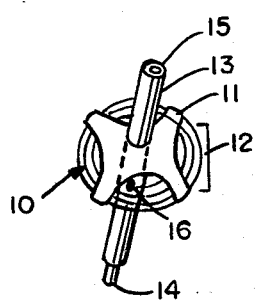
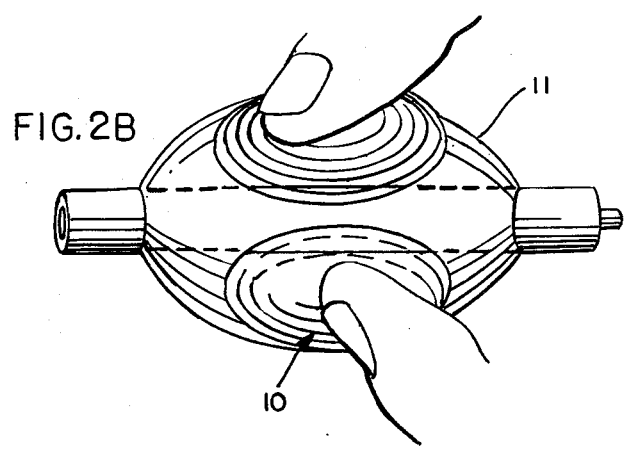
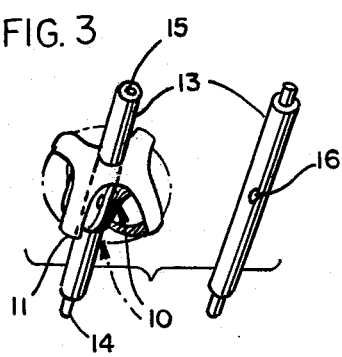
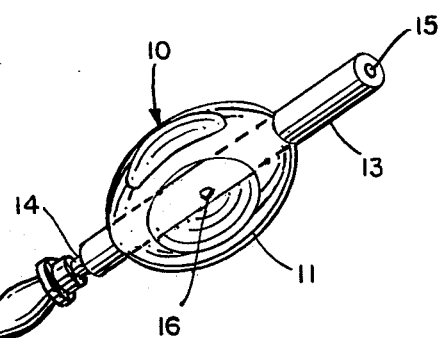
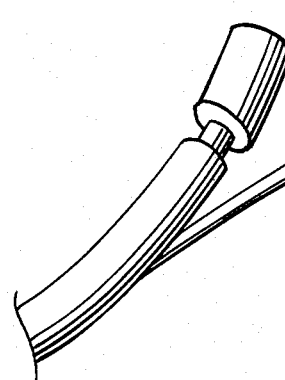

EXTERNAL PRESSURE-VOLUME MONITOR FOR ENDOTRACHEAL CUFF

BACKGROUND AND SUMMARY

An air-filled endotracheal cuff seals the tracheal tube within the lumen of the trachea to prevent leak during inflation and to prevent entry of secretions from the upper airway into the trachea and lungs. Present-day endotracheal tubes feature an air inflation channel and small-bore tubing leading to the cuff and a so-called pilot balloon in the proximal segment of the inflation channel to provide external visible proof of the state of cuff inflation. However, current pilot balloons no longer provide this proof. Unfortunately, recently marketed cuffed endotracheal tubes have abandoned the original purpose of the pilot balloon by substituting a "miniature" polymer molded bulb which remains normally in expanded position at zero pressure. The walls of such polymer bulbs are inelastic and are too thick to collapse with cuff deflation and consequently fail to give any indication of the patient's ventilator has failed to inflate the lungs.

Therefore, the several purposes of this invention are to create a pressure-volume monitor to continuously indicate externally the status of inflation of the endotracheal cuff. Secondly, to utilize an elastomer for the balloon of the monitor whose thin walls are collapsible and expandable to provide an appreciable change in balloon size with changes in internal air pressure, thereby to result in a sensitive and obvious indication of both pressure and volume in the cuff system without the use of an overflow spill valve. Thirdly, it shall be the purpose of this invention to control the elastomer balloon wall thickness to insure the sensitive response in the appropriate and safe range of cuff pressure, giving obvious evidence of pressures above 15 centimeters of water, which is the critical cuff pressure above which tracheal injury results. Fourthly, the invention shall provide means for identifying a normal level of pressure and volume in the endotracheal cuff by direct inspection of balloon size in relation to the structure of the rigid cage which surrounds the balloon, such containment of the balloon by the cage serving subsequently as a visual reference to discover minute changes in balloon size as long as the patient's trachea remains intubated. Finally, the invention shall include means to alert nursing personnel by warning and alarm signals to the hazards related to either excess cuff pressure or leaking collapsed cuffs which may in turn result in failure of lung inflation by a mechanical respirator. Attainment of these several features results in a practical, inexpensive, durable, mechanical pressure-volume sensor which continually and conveniently reveals the safety and security of the state of inflation of the endotracheal cuff.

This invention replaces the contemporary pilot balloon of only 0.5 to 1.0 milliliter volume with a reliable pressure-volume monitor capable of continuous indication not only of the state of collapse or expansion of the endotracheal cuff but, more importantly, indicating accurately the level of pressure within the cuff, permitting early discovery by attending personnel of both leakage and excessively high cuff pressure before problems arise. The balloon wall of the monitor is an appropriately thin elastomer. The size of the balloon resembles that of the cuff itself, about 20 milliliter volume at 10 centimeters of water and 30 milliliter volume at 20 centimeters of water, this pressure-volume behavior being the basis for a sensitive indication of system pressure by virtue of the balloon just contacting the cage structure at 10 centimeters of water pressure and bulging through windows in the cage at 20 centimeters of water, therefore, the balloon is constructed of silicone or Kraton rather than PVC, or other inelastic polymers. Non-elastic properties of polymers fail to reveal overexpansion of cuffs. Thus, the contemporary "PVC pilot balloons" fail to reveal visible evidence of excessive harmful cuff pressures or of zero pressure. Thus, the pressure-volume monitor of this invention utilizes a balloon with a specific wall thickness such that 20 ml of air produces a characteristic internal pressure. For example, three different balloons of different wall thickness produce pressures of 10 cm of water, 50 cm of water and 200 mm of mercury when filled to occupy the same space within the cage. By attaching the monitoring balloon in series with the inflation channel and endotracheal cuff of any endotracheal tube, one may identify whether the cuff pressure is harmful or benign, and thereby avoid the serious complications arising when high lateral wall pressures are exerted against the wall of the trachea. These cited pressures unfortunately cover the range of cuff pressures typical of currently available cuffed endotracheal tubes cuffs, the latter two being harmful.

On the other hand, the safety of the tracheal seal, during lung inflation, dependent upon the integrity of the cuff, particularly in patients on mechanical ventilation, may be simply and routinely monitored by inspecting the system of this invention. Nursing personnel may visually inspect the monitor, may palpate with two fingers the balloon's pressure, or may be allerted by pressure sensitive switches in the monitor to a failure of the cuff system.

The foregoing and other objects and advantages of the invention will be set forth in or are apparent from the following description and drawings.

DRAWINGS

In the figures:

FIG. 1 is a perspective view of the balloon monitor within its surrounding rigid cage under a state of normal inflation with the balloon fully occupying the cage and contacting its longitudinal struts.

FIG. 2a is a lateral view of the monitor showing the shape of the four windows in the cage, each sized to admit an adult's fingertips as shown in FIG. 2b.

FIG. 3 is a perspective view of the monitor with the balloon collapsed against the central thick-wall core tubing having a single orifice at its center capable of being occluded by fingers in order to by-pass inflation of the balloon during inflation or deflation of the endotracheal cuff. FIG. 3 also depicts the result of air leakage in the cuff system as a result of a defect in the cuff seal or of a prolonged diffusion of air from the cuff illustrating how the monitor may alert attending personnel in a life threatening situation.

FIG. 4 is a perspective view of the monitor attached to the proximal end of the cuff inflation tubing of a conventional endotracheal tube, the entire pneumatic system being inflated to a pressure of 10 centimeters of water resulting in complete and proper filling by the balloon of the space within the cage.

FIG. 5 is a lateral view similar to FIG. 4 in which the entire pneumatic system has been over-inflated to result in bulging of the balloon through the oval windows of the cage, thereby indicating harmfully excessive intracuff pressures.

Figure 6:
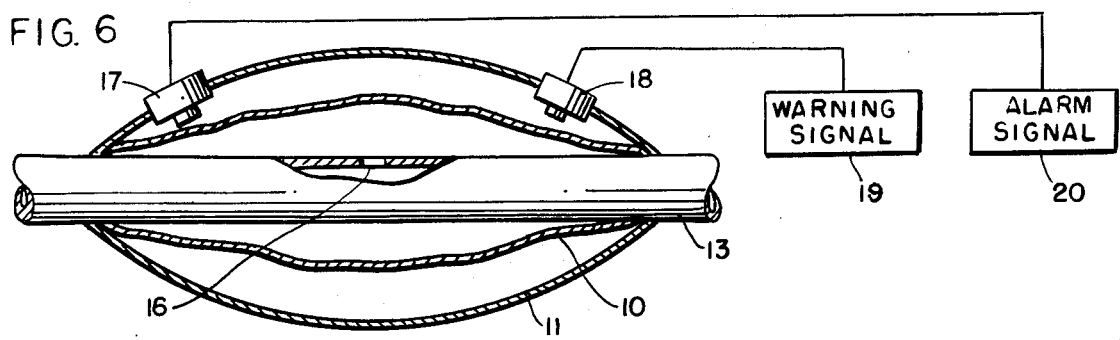

FIG. 6 is a lateral view partially in section of an alternative embodiment of the monitor showing micro-switches enlarged for clarity providing an alarm signal or a warning signal in the event of cuff under-inflation or cuff over-inflation.

Figure 7:
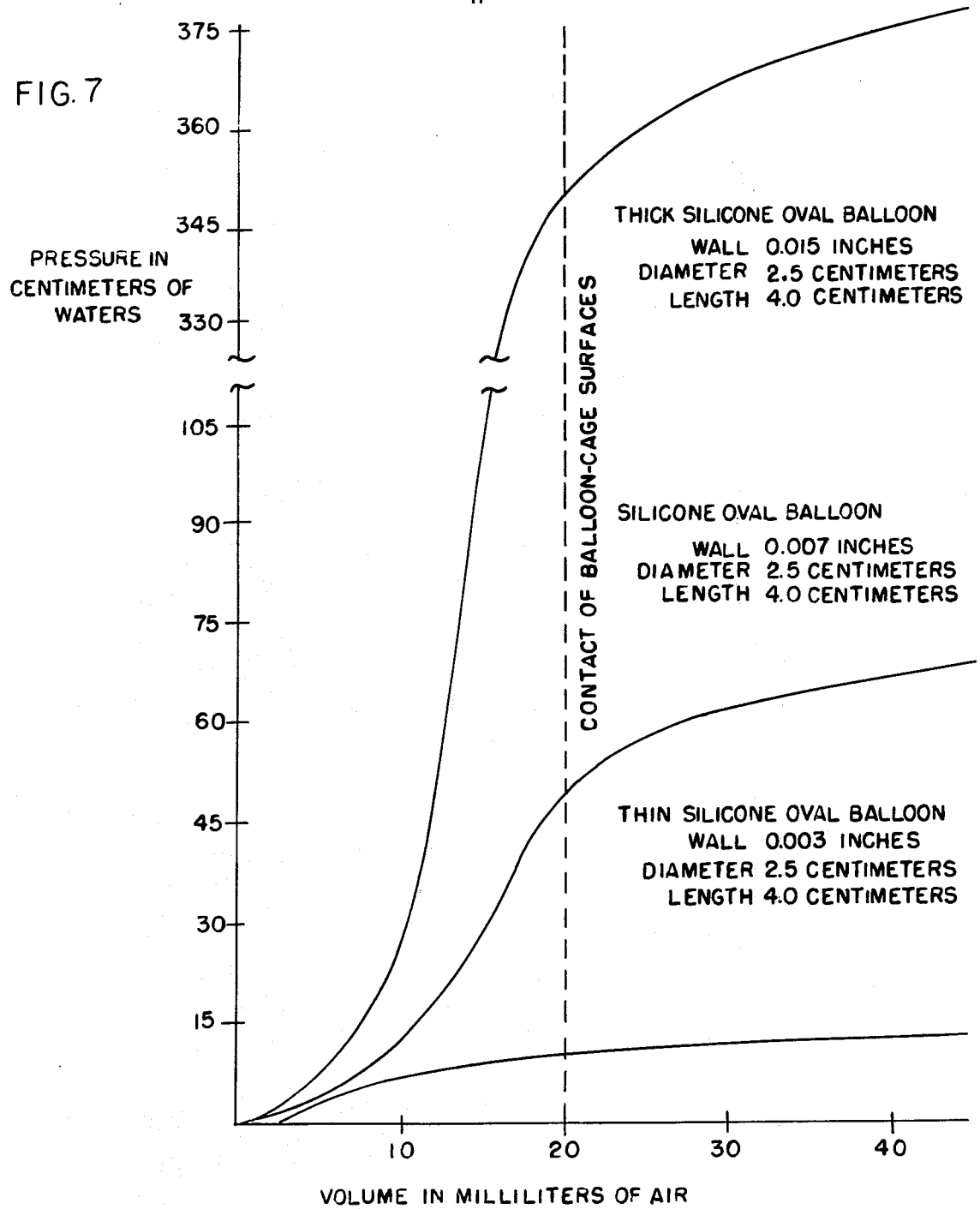

FIG. 7 is a graphic illustration of the pressure-volume relationship of balloons of varying wall thicknesses.

DETAILED DESCRIPTION

Referring to FIG. 1, the balloon 10 is constructed of a thin elastomer with a configuration and size approximating that of an endotracheal cuff. An ovoid cage 11 is constructed of rigid, strong-light-weight metal or plastic, to surround the balloon 10 so that the cavity defined by the cage is fully occupied by the balloon at the normal state of inflation with 20 milliliters of air and 10 centimeters of water pressure. The four oval windows 12 in the cage 11 provide for convenient inspection of the balloon wall with reference to the fixed volume of the cage 11 and allow fingertip palpation to sense balloon pressure. A central core tube 13 traverses the balloon interior longitudinally with an end-to-end distal end consisting of a male fitting 14 to fit into the valved tip of the inflation channel of a contemporary cuffed endotracheal tube. At the proximal end of the core tubing 13 a valved standard female inlet 15 is mounted. A small orifice 16 in the core tubing 13 is marked and visible through the transparent balloon wall, to facilitate fingertip occlusion of the orifice during inflation of the cuff, for momentary by-pass of the monitoring balloon. Release of the occlusion of orifice 16 allows the transfer of air retrograde from the endotracheal cuff to reveal the state of inflation thereof. To attain proper cuff inflation at safe pressure, increments of air are introduced through valved inlet 15 until the balloon 10 fully occupies the cage 11. Respective volumes of 20 milliliters, 30 milliliters, and 10 milliliters produce an indication of their magnitude by the size of the balloon 10 as illustrated in the Figures. Corresponding pressures in these states of inflation are 10 centimeters of water in FIG. 4, 17 centimeters of water in FIG. 5 and 0 centimeters of water in FIG. 3.

The wall of the elastomer balloon 10, shown collapsed in FIG. 3, has a wall thickness of three thousandths of an inch which produces a balloon pressure of 10 centimeters of water with injection of 20 milliliters. Substitution of an elastomer balloon of equal size with a wall thickness of seven thousandths of an inch provides the monitor with a balloon which identifies 50 centimeters of water pressure upon injection of 20 milliliters of air. A wall thickness of fifteen thousandths of an inch produces a balloon pressure of 350 centimeters of water with injection of 20 milliliters.

Accordingly, wall thickness determines the specific pressures for a series of monitors for each of which a specific pressure produces full expansion of the monitoring balloon. Therefore, an appropriate group of such monitors with different thicknesses of their respective balloons may be calibrated and specifically labeled in centimeters of water at normal volume within each cage to monitor specific pressure levels. The group of monitors can be selected to cover the appropriate ranges of contemporary endotracheal cuffs which vary from 10 centimeters to 260 centimeters of water pressure.

For elastomer balloons the accuracy of a number of specimens used in the monitor is reproducible within ±5 percent of the average value. The use of polymer balloons for the monitor is without merit as they fail to exhibit proportional volume changes in pressure.

The balloon monitor supplements the safe care of the intubated patient by providing an external visual object for attending personnel to observe to know whether the degree of cuff inflation is satisfactory, whether the cuff has leaked or otherwise lost volume, or whether, through error, the cuff has been overinflated to result in harmful pressures. Use of this invention may therefore reduce or eliminate several of the hazards of prolonged tracheal intubation in intensive care patients by providing the means to prevent the common cause of the critical tracheal damage which results from excessive endotracheal cuff pressures and to determine cuff failure which may result in a failure of a mechanical ventilator.

Since both prolonged overinflation and temporary underinflation of the endotracheal-tube cuff often results in catastrophic problems or death of ICU patients, means are also described here to provide an alarm signal in the event of cuff underinflation (as shown in FIG. 3) and a warning signal for overinflation (as shown in FIG. 5) of the cuff-monitoring balloon system. The means disclosed (as shown in FIG. 6) consists of conventional sensitive micro-switches which respond electrically to pressure contact. The micro-switches are mounted between the balloon wall and the interior surface of the surrounding cage in the top or bottom of the cage, arranged to respond to a release of balloon contact against the inner surface of the cage and thereby activating electrically an alarm or warning annunciator nearby or to respond to excess balloon pressure with another micro-switch which identifies excessive pressure in the balloon and the endotracheal cuff by activating electrically an alarm or warning annunciator at the nursing station.

While in the foregoing specification a detailed description of the invention has been set forth for purposes of illustration, variation of the details herein given may be made by those skilled in the art without departing from the spirit and scope of this invention.

I claim:

1. A monitoring accessory for use with a cuffed endotracheal tube adapted for connection to a proximal inlet of a cuff inflation channel of said tube comprising:
   a thin-walled, collapsible-expandable elastic balloon, said balloon having an injection port and freely communicating with said endotracheal cuff through said cuff inflation channel of said endotracheal tube; and
   a rigid cage having a pair of spaced end portions joined by a plurality of longitudinally extending struts defining a plurality of windows, said windows being disposed about the periphery of said cage to provide a volume reference for determining the state of inflation of said endotracheal cuff, said cage housing said balloon therein and defining a cavity having a shape generally conforming to the freely inflated shape of said balloon and having a fixed volume which is fully occupied by said balloon under a normal level of inflation of said endotracheal cuff, said balloon being disposed within said cavity in a manner permitting visual and fingertip perception through said windows of any departure from said normal level of inflation of said endotracheal cuff;

whereby said monitoring accessory serves as a simple system for continuously monitoring the unseen condition of said endotracheal cuff.

2. The monitoring accessory of claim 1 wherein a central tube extends end-to-end through said balloon and said spaced end portions of said rigid cage, said tube having an orifice intermediate the ends thereof in communication with said balloon, said balloon being transparent and said orifice being visible to facilitate fingertip occlusion thereof through at least one of said windows to permit inflation of said endotracheal cuff prior to said balloon, said central tube including means for connection to said proximal inlet of said cuff inflation channel and means for connection to an external source of air.

3. The monitoring accessory of claim 1 including a micro-switch placed between the outer surface of said balloon and the inner wall of said cage responsive to under-inflation of said balloon, said micro-switch being connected to a warning or alarm signal.

4. The monitoring accessory of claim 1 including a micro-switch placed between the outer surface of said balloon and the inner wall of said cage responsive to over-inflation of said balloon, said micro-switch being connected to a warning or alarm signal.

* * * * *